United States Patent [19]

Eyal et al.

[11] Patent Number: 6,037,480
[45] Date of Patent: Mar. 14, 2000

[54] PROCESS AND COMPOSITIONS FOR THE RECOVERY OF ASCORBIC ACID

[75] Inventors: Aharon M. Eyal, Kibbutz Ramat Rachel; Betty Hazan, Jerusalem, both of Israel

[73] Assignee: Yissum Research Development Company of The Hebrew University of Jerusalem, Jerusalem, Israel

[21] Appl. No.: 08/952,491

[22] PCT Filed: May 31, 1996

[86] PCT No.: PCT/US96/08093

§ 371 Date: Feb. 23, 1998

§ 102(e) Date: Feb. 23, 1998

[87] PCT Pub. No.: WO96/38433

PCT Pub. Date: Dec. 5, 1996

[30] Foreign Application Priority Data

May 31, 1995 [IL] Israel .......................................... 113928

May 31, 1995 [IL] Israel .......................................... 113929

[51] Int. Cl.[7] .................................................. C07D 307/62
[52] U.S. Cl. ........................... 549/315; 252/364; 435/126
[58] Field of Search ............................ 549/315; 252/364; 435/126

[56] References Cited

U.S. PATENT DOCUMENTS

| 3,944,606 | 3/1976 | Rieger et al. | 260/535 |
| 4,275,234 | 6/1981 | Baniel et al. | 562/584 |

*Primary Examiner*—Bernard Dentz
*Attorney, Agent, or Firm*—Foley & Lardner

[57] ABSTRACT

The invention provides an extraction process for the recovery of ascorbic acid from an aqueous feed solution containing the acid at a concentration of less than 0.7 mol/kg.

14 Claims, 4 Drawing Sheets

PROCESS AND COMPOSITIONS FOR THE RECOVERY OF ASCORBIC ACID

This application is a 371 of PCT/US96/08093 filed May 31, 1996.

The present invention relates to a process for the production of ascorbic acid. More particularly, the present invention relates to the recovery of ascorbic acid from aqueous solutions containing the same in dilute concentrations.

As described, e.g., in Kirk-Othmer's *Encyclopedia of Chemical Technology*, Third Edition, ascorbic acid (L-ascorbic acid, L-xylo-ascorbic acid, L-threo-hex-2-enonic acid τ-lactone) is the name recognized by the IUPAC-IUB Commission on Biochemical Nomenclature for vitamin C. The name implies the vitamin's antiscorbutic properties, namely, the prevention and treatment of scurvy. L-ascorbic acid is widely distributed in plants and animals. The pure vitamin ($C_6H_8O_6$, mol. wt. 176.13) is a white crystalline substance derived from L-gulonic acid, a sugar acid, and synthesized both biologically and chemically from D-glucose.

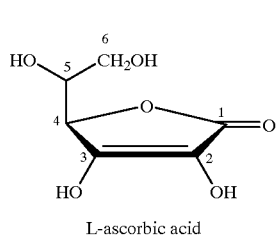

L-ascorbic acid (1)

Although natural and synthetic vitamin C are chemically and biologically identical, in recent years a limited amount of commercial isolation from vegetable sources, e.g., rose hips, persimmon, citrus fruit, etc., has been carried out to meet the preference of some persons for vitamin C from natural sources. L-ascorbic acid was the first vitamin to be produced in commercial quantities, and manufacture is based on the well-known Reichstein and Grussner synthesis, which involves the steps of hydrogenation of D-glucose to D-sorbitol; fermentation (oxidation) to L-sorbose; acetonation to bis-isopropylidene-α-L-sorbofuranose; oxidation to bis-isopropylidene-2-oxo-L-gulonic acid, and hydrolysis, rearrangement and purification to L-ascorbic acid.

A direct fermentation of glucose to ascorbic acid would be very attractive, saving on operations and on expensive reagents, in addition to its being derived from a natural fermentation process, as opposed to a synthesis involving chemical steps. There are indications that such direct fermentation to ascorbic acid is feasible. Yet industrial production of ascorbic acid through direct fermentation seems impractical, in view of the low product concentration in the fermentation liquor, which normally is in the range of less than 0.7 mol/kg. Purifying the ascorbic acid by conventional methods would result in a purified product of concentrations similar to those in the fermentation liquor. Due to its high solubility in water, the cost of ascorbic acid crystallization by water evaporation would be prohibitive.

Several methods were proposed for combining purification of carboxylic acids with their concentration. In the case of citric acid, it is achieved by the addition of lime to crystallize calcium citrate, which has very low solubility in water. This salt is separated, washed and acidulated with sulfuric acid. Purified and concentrated citric acid is obtained. This method is not applicable for ascorbic acid, as its alkali and alkali earth salts are highly soluble.

A process was proposed in which carboxylic acids were extracted and then displaced from the extractant by a solution of concentrated mineral acids. Both liquid (long chain amines) and solid (resins carrying amine groups) anion exchangers could be considered for this purpose. The purity of the displaced carboxylic acid depends on the preference of the extractant to the mineral acid. Such a process might be applicable for ascorbic acid separation and concentration, provided that the extractant is strong enough to reach high extraction yield, that it shows high preference to the displacing acid, and that the ascorbic acid is stable at the high acidity of the displacing solution.

The regeneration of the anion exchanger would require neutralization by a base. Using HCl as the displacing acid and distilling it of the extractant was proposed, but the high temperatures required and the extractant's decomposition at these conditions are prohibitive. If the anion exchanger is represented by B, the ascorbic acid in the fermentation liquor and in the pure form are $AA_F$ and $AA_P$, respectively, the displacing acid is HCl, and the neutralizing base is NaOH, the equations of the process stages and of the overall reaction are as follows:

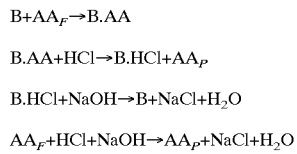

Reagents are consumed, and a by-product salt of no (or negative) value is produced.

Thus, despite the widely felt need for a more attractive process to meet the exceedingly high demand for ascorbic acid, to date no such process has been proposed or commercialized.

In 1976, there issued British Patent 1,426,018 and in 1981 there issued the corresponding U.S. Pat. No. 4,275,234, directed to the recovery of acids from aqueous solutions. In said patents, there are exemplified the recovery of citric acid, lactic acid, oxalic acid, and phosphoric acid from an aqueous solution of the same acid; in fact, said U.S. Patent is specifically limited in its claims to the recovery of one of said four acids.

While the process of the present invention as defined herein formally falls within the scope of said aforementioned British patent, the relevant teachings of which are incorporated herein by reference, and in this sense constitutes a selection therefrom, as will be explained further below, not only do said patents neither teach, suggest, nor exemplify the applicability of said process to the recovery of ascorbic acid, but in fact, from a careful analysis of said patents, one would not expect said process to be feasible for the recovery of ascorbic acid, as is also evidenced by the fact that nineteen years have passed from the publication of said British patent without any person skilled in the art either suggesting or applying said process to ascorbic acid recovery.

Referring now to said patents and the teachings thereof, one finds that the process taught therein utilizes the effect of temperature on phosphoric and carboxylic acid extraction by amine-based extractants. The term "amine" as used herein means water-immiscible amine, with a total of at least 20 carbon atoms on its chains. Said patents teach that such amine-based extractants (ABE) lose much of their extraction efficiency upon temperature elevation. This loss of efficiency is referred to as "temperature sensitivity of extraction" (TS).

The magnitude of this TS can be represented by the ratio of the distribution coefficient at the lower temperature ($D_{T1}$) and the distribution coefficient at the higher temperature ($D_{T2}$). High TS provides for the purification and the concentration of carboxylic acids through altering the temperature between extraction and back-extraction. The acid is extracted from the fermentation liquor by an ABE at low temperature, and is then back-extracted with water at an elevated temperature. The aqueous solution obtained from that back-extraction is, in many cases, more concentrated than in the fermentation liquor. This process is referred to herein as the "temperature swing process" (TSP). The attraction of such processes is in the fact that the sole energy consumption is that of sensible heat, which saves a lot of the latent heat of water evaporation in the final concentration.

As explained in U.S. Pat. No. 4,275,234:

"The concepts of "lower temperature" and "higher temperature" are not understood in absolute terms. What matters . . . is the temperature differential. This will have to be at least 20 degrees (centigrade), both for operation convenience and in order to make both the extraction and the back-extraction as complete as possible. The extraction may be carried out at temperatures as low as near the freezing point of the aqueous acid solution and the temperature of the back-extraction may be at or near the boiling point of the extract or the water at atmospheric pressure, or if the back-extraction is carried out under elevated pressure, at an even higher temperature, always on condition that the temperature and pressure are so chosen that the amine remains in the organic phase. In many cases the extraction can be carried out at or near room temperature, and the stripping operation at a temperature of about 20 to 40 degrees (Centigrade) above room temperature. As a rule, the stripping operation is the more effective, the higher the stripping temperature, but the extraction and stripping temperatures will be selected in individual cases in accordance with practical factors, such as corrosion-resistance and the costs of the equipment, costs of heating and cooling of the streams of the acid solution, the extract and the extractant, the required concentration of stripped acid, etc.

"If the aqueous liquid used for stripping the extract is water, the back-extract is an aqueous solution of the free acid. If desired, the back-extracting operation may be so conducted that the back-extract is an aqueous solution of a salt of the extracted acid. For example, back-extraction with an aqueous alkali metal (in this context "alkali metal" includes ammonium) hydroxide solution yields an aqueous solution of the corresponding alkali metal salt of the extracted acid. Or the aqueous back-extracting liquid may be, for example, an alkali metal chloride solution. In this case, too, the back-extract contains the corresponding alkali metal salt of the extracted acid while the amine in the extractant is converted into its hydrochloride. This will thus have to be decomposed, e.g. by treatment with calcium hydroxide, for reconstituting the extractant. Sometimes it is advantageous to perform first a back-extraction with water in order to recover the major part of the acid in the free state. The residue of acid remaining in the solvent extract can then be back-extracted with an alkali metal hydroxide or salt solution.

"The most favourable selection of the temperature of the extracting operation and of the compositions of the extractant, as regards both the amine and the solvent, will also be determined according to the given condition of particular cases, e.g., the kind of acid, its concentration in the original aqueous solution, the impurities present in that solution. The major aim in both the extracting and stripping operations will be to achieve as favourable a distribution coefficent as possible for the distribution of the acid between the aqueous and organic phases. In the extraction operation, this has to be in favour of the extractant; in the stripping operation, in favour of the aqueous phase."

As stated above, the characterizing feature of said patents is that back-extraction is performed at a temperature higher than that of the extraction. For certain acids, there is shown efficient extraction at about room temperature. Back-extraction at about 100° C. provides for a back extract, the concentration of which is similar to, or even higher than, that of the feed. In fact, a major part of citric acid production in the world is based on this process, using tridodecyl amine as the primary extractant and 1-octanol as the enhancer [Kirk-Othmer, *Encyclopedia of Chemical Technology*, 4th Ed., Vol. 6, p. 364].

The degree of product concentration in the TSP (the uphill pumping effect) depends strongly on the magnitude of the TS. The thermodynamic explanation for the TS is not clear enough. One could suggest that as the extraction process is exothermic, equilibrium is shifted backwards on temperature elevation. That would, however, be too simplistic. Thus, the most exothermic extraction is that of strong mineral acids, but no TS is found for their extraction. To the best of our knowledge, this complex phenomenon was not fully explained in said patents, and no tools were provided for predicting the magnitude of TS from the structure of the extracted acid.

The magnitude of the TS for extraction of various carboxylic acids by an extractant composed of 0.5 mol/kg trilauryl amine (Henkels Alamine 304) and 10% octanol in a kerosenic diluent have now been tested. The results are presented below in Table 1:

TABLE 1

The temperature sensitivity of carboxylic acid extraction by 0.5 mol/kg Alamine 304 + 10% octanol in kerosene. The temperature sensitivity (TS) is presented as the distribution coefficient at 30° C., divided by that at 75° C., at various equilibrium aqueous phase concentrations.

| | | TS in Equilibrium with Aqueous Solutions of (mol/kg) | | | |
|---|---|---|---|---|---|
| Acid | pKa | 0.05 | 0.2 | 0.3 | 0.475 |
| Maleic[2] | 1.93 | 1.1 | 1.0 | 1.0 | 1.0 |
| Oxoglutaric[2] | 2.57 | 2.4 | 1.5 | 1.3 | 1.1 |
| Malonic[2] | 2.83 | 3.6 | 1.5 | 1.3 | 1.1 |
| Tartaric[2] | 3.01 | 3.4 | 3.2 | 2.7 | 2.4 |
| Citric[3] | 3.13 | 6.0 | 3.1 | 2.6 | 2.2 |
| Malic[2] | 3.22 | 4.0 | 4.3 | 4.0 | 4.0 |
| Gluconic[2] | 3.75 | 2.1 | 2.3 | 2.4 | 2.6 |
| Lactic[1] | 3.86 | 2.5 | 2.4 | 2.4 | 2.2 |
| Succinic[2] | 4.2 | 4.3 | 4.0 | 4.0 | 4.1 |
| Glutaric[2] | 4.4 | 3.9 | 4.5 | 4.5 | 4.4 |
| Acetic[1] | 4.76 | 2.3 | 2.4 | 2.4 | 2.4 |
| Butyric[1] | 4.81 | 2.1 | 2.0 | 2.0 | 1.8 |
| Isobutyric[1] | 4.84 | 1.9 | 1.5 | 1.4 | 1.1 |
| Propionic[1] | 4.87 | 1.7 | 1.5 | 1.3 | 1.1 |

[1]Monocarboxylic acid
[2]Dicarboxylic acid
[3]Tricarboxylic acid

One can see that the TS may depend on the equilibrium concentration of the acid in the aqueous phase and that it varies significantly from one acid to the other. No linear correlation is found, however, between the TS and the strength of the acid or another defined characteristic thereof. The strongest TS was found for citric acid at the low concentration of 0.05 mol/kg; some dicarboxylic acids show a higher TS than their monocarboxylic analogues. That might indicate a tendency of TS to increase with an increase in the number of carboxylic groups. Isolating this parameter from the others is difficult.

Extraction of strong mineral acids by ABE is very efficient, reaching stoichiometric levels already at equilibrium with dilute aqueous solutions. That is true even for the weakest straight chain aliphatic amines, the tertiary ones reaching the stoichiometric extraction of 1 mol of HCl per mol of amine in equilibrium with aqueous solutions of about 0.5%. High efficiency is also found in extracting strong carboxylic acids having a pKa less than 2.5. The efficiency is, however, much lower on extracting weaker carboxylic acids by tertiary amines in a kerosenic diluent. Said low efficiency is particularly pronounced in the low concentration range. In order to avoid low yields of extraction, extraction enhancers are introduced into the extractant.

It is well-known that polar and protic compounds provide for enhancement of acid extraction by amines. These compounds may act as acid extractants by themselves, but are much weaker extractants than the amines. Extractants comprising amines and enhancers show synergistic effects in most cases, i.e., acid extraction by such extractants is much higher than the added contribution of the components.

In the description of the invention herein, and to avoid confusion, the term "primary extractant" will be used for long-chain amines used for extractions, and the term "enhancer" will be used for polar and protic extractant components, the extraction power of which is smaller than that of the primary extractant. Suitable enhancers are polar, and preferably protic compounds, including alkanols, ketones, aldehydes, esters and ethers of various molecular weights.

Desired extractants should provide high efficiency in extraction (relatively low extractant volumes, a small number of extractant stages and high yields), high selectivity, low water miscibility, low toxicity (particularly for food grade products), and efficient stripping of the extracted acid from the extract. The acid can be removed from the extract through interaction with an aqueous solution of a base to form its salt. In most cases, however, the acid is the required product rather than the salt, and acid recovery from the extract is performed by back-extraction with water or by distillation, where feasible.

As is known, high efficiency in extraction from the feed and high efficiency in stripping are conflicting requirements. Back-extraction of the extracted acid from a strong extractant requires high volumes of water and results in a very dilute aqueous solution of the acid (back-extract). The high cost of product concentration may make the whole process impractical. Distillation from a strong extractant requires high temperatures and may result in the decomposition of the acid and/or the extractant.

Extraction enhancers are polar and, preferably, protic compounds that have very low extraction capacity on their own, but significantly improve the extraction efficiency of ABE. The enhancement is explained by stabilization through salvation of the amine-acid ion pair. Octanol is used as an enhancer in the industrial TSP for production of citric acid.

Extraction enhancers have, however, an adverse effect on TSP, as the temperature sensitivity decreases with an increase in enhancer content. Such an effect is shown below in Table 2:

TABLE 2

The dependence of the temperature sensitivity of citric acid extraction by amine-based extractant on amine concentration, enhancer (octanol) concentration, and on equilibrium aqueous phase concentration.
The temperature sensitivity is presented as the ratio of distribution coefficient at 30° C. and 75° C.).

| Amine | Octanol | D30/D75 at Aqueous Concentration | | |
|---|---|---|---|---|
| mol/kg | mol/kg | 0.02 | 0.5 | 1.5 |
| 0.2 | 0.31 | 30.0 | 6.4 | 2.1 |
| 0.2 | 0.62 | 10.8 | 2.0 | 1.3 |
| 0.2 | 2.0 | 4.9 | 1.3 | 1.1 |
| 0.5 | 0.31 | 31.3 | 3.7 | 1.4 |
| 0.5 | 0.62 | 4.6 | 1.5 | 1.1 |
| 0.5 | 2.0 | 2.1 | 1.1 | 1.05 |
| 1.0 | 0.31 | 10.5 | 1.2 | 1.07 |
| 1.0 | 0.62 | 4.9 | 1.1 | 1.01 |
| 1.0 | 2.0 | 1.8 | 1.08 | 1.03 |

There is, therefore, a trade-off between extraction efficiency and the magnitude of the TS. Thus, aiming at a higher degree of product concentration in the process leads to lower efficiency, particularly at the low concentration end, resulting in lower recovery yields, i.e., higher product losses. The absolute losses, expressed, for example, by the product concentration in the raffinate, depend on the shape of the distribution curve at the low concentration end. The proportional loss is mainly determined by the concentration of the acid in the fermentation liquor.

The TSP was implemented for citric acid recovery from fermentation liquors due to the unique, favorable combination of very high temperature sensitivity (the highest reported so far) and the relatively very high concentration of citric acid in the fermentation liquor, typically 16–18%. Even at these unique conditions, the enhancer level should be reduced to a minimum. R. Wennerstern [*J. Chem. Tech. Biotec.,* No. 33B, pp. 85–94 (1983)] studied the effect of the various extractant parameters and concluded that hydrocarbons are the preferred diluents, as polar diluents reduce the temperature effect. Cooling below ambient temperature or preconcentration of the fermentation liquor [U.S. Pat. No. 4,994,609] are required to avoid major product losses.

The above limitations brought Bauer, et al. to conclude, in 1989, that a TSP is not even economic for citric acid, and that displacement of the extracted acid by another acid (acetic) is preferable [Bauer, et al., *Ber. Bunsenges. Phys. Chem.,* Vol. 93, pp. 980–984 (1989)].

It is important to note at this juncture that ascorbic acid does not carry a carboxyl group and therefore it is not a carboxylic acid, nor is it a mineral acid. Consequently, patents and disclosures which are directed to processes for treating or recovering carboxylic and/or mineral acids do not include ascorbic acid within their scope.

According to its pKa, ascorbic acid is quite weak, being more than an order of magnitude weaker than citric acid. Its low acidity and high hydrophilicity (since it carries 4 hydroxyl groups) reduce its extraction efficiency.

Extraction efficiency is determined by the distribution coefficient dependance on the aqueous phase concentration (the shape of the distribution curve). The distribution coefficient at the high concentration end determines the maximal loading of the extractant, and thereby, the volume of the recycled extractant. The distribution coefficient at the low concentration end determines the ability to approach complete extraction, and thereby, the extraction yield. For extraction of a component from a dilute feed, the yield of extraction is very important. Reaching high yields in extracting from a dilute feed a relatively weak and highly hydrophilic acid, such as ascorbic acid, would require high enhancer levels.

Test results in Table 1 above show that the strongest temperature sensitivity so far is found for citric acid, and that this temperature sensitivity drops with a decreasing number of carboxyl groups. Nothing in these results, or in those found in the literature, indicates that ascorbic acid would show a higher temperature sensitivity than citric acid.

Even if ascorbic acid extraction had the temperature sensitivity of citric acid extraction, one would not consider its recovery from dilute solutions in the TSP, due to the fact that at low enhancer levels, the losses would be extremely high. On the other hand, at high enhancer levels, the temperature sensitivity decreases. Thus, the major advantage of the process, i.e., recovering the product at a concentration substantially higher than that of the fermentation liquor, would be lost.

In light of the above, it was extremely surprising to discover that the temperature sensitivity of ascorbic acid extraction by amine-based extractants is very high and is maintained, even at high enhancer levels. Based on this discovery, there is now provided, according to the present invention, a process for the recovery of ascorbic acid from an aqueous feed solution containing said acid at a concentration of less than 0.7 mol/kg, comprising extracting said ascorbic acid with a water-immiscible organic extractant composition comprising (a) at least one secondary or tertiary alkyl amine in which the aggregate number of carbon atoms is at least 20, as a primary extractant, and (b) a polar extraction enhancer compound; wherein said extractant composition comprises at least 2 moles of said polar extraction enhancer compound per one mole of primary extractant; separating said ascorbic acid-containing organic extractant composition from residual aqueous solution, and subjecting said ascorbic acid-containing organic extractant composition to a stripping operation with aqueous solution at a temperature of at least 20° C. higher than the temperature at which said extraction is carried out; whereby there is obtained an aqueous solution of ascorbic acid in which the concentration of ascorbic acid is higher than its concentration in said aqueous feed solution.

The process of the present invention is so effective that in preferred embodiments thereof as described hereinafter, said ascorbic acid can be recovered from an aqueous feed solution containing said acid at a concentration of less than 0.5 mol/kg.

Extractants comprising relatively strong amines as the primary extractant, show nearly no temperature sensitivity on the efficiency of extracting strong mineral acids. It was, however, found that relatively weak amines do show such effect. An example of such weak amines is the sterically-hindered, branched chain amines with branching on a carbon close to the nitrogen atom [Eyal, et. al., *Solvent Extraction and Ion Exchange,* Vol. 9, pp. 195–236 (1991)]. These amines are weaker by more than two orders of magnitude than straight chain amines, and weaker than branched chain amines with branching far from the nitrogen atom. Such amines are too weak to extract most weak acids and are not suitable for use as primary extractants in the present invention. For simplicity of language, the term "branched chain amines" will be used here just for sterically hindered, relatively weak amines with branching close to the nitrogen atom.

Branched chain amines are too weak to extract many of the carboxylic acids, particularly hydroxycarboxylic acids. Straight chain amines are much more efficient, but complete extraction without resorting to high cooling costs requires the use of extraction enhancer. This is particularly true for extraction from dilute feed solutions. Yet, the stronger is the enhancer and the higher its contents, the lower is the sensitivity of extraction efficiency to temperature. Thus, amine-based extractants, comprising relatively strong enhancers at high proportions of enhancers, show high efficiency in extraction, but lose most of the advantage in back-extraction at higher temperature, according to U.S. Pat. No. 4,275,234.

According to the known practice, there have been suggested four main options, as well as variations and combinations thereof:

a) Use of a weak enhancer or a strong enhancer, at a minimal concentration required for extraction completion (non-optimal extractant composition in extraction, high extractant volume, many stages in extraction and relatively high losses). This option was chosen for the citric acid production.

b) Increase the temperature span between extraction and back-extraction (expensive cooling and high viscocity in extraction, and expensive heating and thermal degradation in back-extraction).

c) Distill at least part of the enhancer from the extract prior to back-extraction (high energy cost, limitation to volatile enhancers that in most cases have relatively high solubility in the aqueous streams, requiring additional recovery operations).

d) Add to the extract an a-polar solvent that acts as extraction suppressor, and removal of this solvent prior to the use of the regenerated extractant (low efficiency, high energy cost).

In contradistinction to the above options, a further preferred aspect of the present invention is based on the discovery that polar organic compounds with steric hinderance of the polar group have, at about ambient temperature, an enhancement effect similar to that of similar non-hindered compounds, but lower enhancement effect at elevated temperature. As a result, efficient extraction is achievable using amine-based extractants at about ambient temperature, in combination with convenient amounts of enhancer, while efficient back-extraction is achieved at elevated temperature, without resorting to unduly high temperatures in back-extraction and/or high energy-consuming removal of extractant components, either prior to back-extraction or after it.

Furthermore, it is well known that enhancer-containing extractants provide for more efficient extraction, but at the cost of reduced temperature sensitivity of the extracting power. The advantage of enhancer application in the extraction may be out-balanced by the reduced temperature sensitivity. Thus, for extraction of an acid from an aqueous feed of a relatively high acidity, particularly if incomplete extraction can be tolerated, non-enhanced (or slightly enhanced) extractants are preferred. On the other hand, in extraction from dilute aqueous solutions of acids, and particularly in extraction from aqueous solutions of relatively high pH, an enhanced extractant is essential for efficient extraction (alternatively, a non-enhanced, very strong amine can be used as a primary extractant, but stripping is impractical for such extractants).

In light of the above, there is now provided, according to preferred embodiments of the present invention, a process for the recovery of ascorbic acid from an aqueous feed solution containing said acid at a concentration of less than 0.7 mol/kg, comprising extracting said ascorbic acid with a water-immiscible organic extractant composition comprising (a) at least one secondary or tertiary alkyl amine in which the aggregate number of carbon atoms is at least 20, as a primary extractant, and (b) a sterically hindered, polar, organic, extraction enhancer compound having at least 5 carbon atoms, a basicity weaker than that of said primary extractant, and temperature-sensitive, extraction-enhancing properties; wherein said extractant composition comprises at least 2 moles of said extraction enhancer compound per one mole of primary extractant; separating said ascorbic acid-containing organic extractant composition from residual aqueous solution, and subjecting said ascorbic acid-containing organic extractant composition to a stripping operation with aqueous solution at a temperature of at least 20° C. higher than the temperature at which said extraction is carried out; wherein said extraction enhancer compound both enhances the extracting power of said primary extractant composition and facilitates said temperature-sensitive stripping operation, and whereby there is obtained an aqueous solution of ascorbic acid in which the concentration of ascorbic acid is higher than its concentration in said aqueous feed solution.

In said preferred embodiments of the present invention, said sterically hindered, polar, organic extraction enhancer compound is preferably selected from the group consisting of alkanols, carboxylic acids, tertiary amines, or trialkylphosphates, having a sterically hindering substituent attached to the carbon carrying said polar group, or to a carbon which is alpha, beta, or gamma to said carbon.

Polar, and particularly protic, organic compounds act as enhancers of acid extraction by amines, due to their ability to solvate the amine acid ion pair formed on such extraction. Organic compounds suitable for use as enhancers in the present invention have at least one such polar or protic group, the solvating properties of which are hindered by the structure of the molecule. The polar group is preferably a hydroxyl, an ester, an aldehyde, a carboxyl, a ketone, or an amine, or said polar group can comprise a halogen, sulfur, nitrogen or phosphate atom. The hindrance can be achieved through substitution of a hydrogen atom in the alkyl chain by an aliphatic group, i.e., branching on the carbon atom carrying the polar group, or on a carbon which is alpha, beta, or gamma to said carbon.

The enhancer should be a weaker base than the amine used as the primary extractant in the extractant composite. On equilibrating it with a 0.1M aqueous HCl solution in a proportion that provides for enhancer to HCl molar ratio of 2, the aqueous phase pH will remain below 2. on a similar equilibration, with the amine acting by itself as the non-enhanced extractant, the pH of the aqueous phase increases to about 2.5 or higher.

In addition to the primary extractant and the sterically-hindered, polar, organic enhancer compound, the extractant may comprise a water-immiscible, polar or non-polar solvent, for example, aliphatic or aromatic hydrocarbon, hydrocarbons carrying nitro or halo substituents, and alcohols.

In preferred embodiments of the present invention, said sterically hindered, polar, extraction-enhancing compound is selected from the group consisting of secondary or tertiary alkanols, tris-2-ethylhexyl amine, and tris-2-ethylhexyl phosphate.

The present invention also provides an extractant composition for use in a process for the recovery of ascorbic acid from an aqueous feed solution containing said acid or a salt thereof, said composition comprising (a) at least one secondary or tertiary alkyl amine, in which the aggregate number of carbon atoms is at least 20, as a primary extractant; and (b) a sterically-hindered, polar, organic extraction enhancer compound having at least 5 carbon atoms, a basicity weaker than that of said primary extractant, and temperature-sensitive, extraction-enhancing properties.

In preferred embodiments of the present invention, said extraction composition comprises at least 3 moles of said polar extraction enhancer compound per one mole of primary extractant.

In especially preferred embodiments of the present invention, said stripping action effects the back-extraction of at least 80% of the ascorbic acid contained in said organic extractant composition.

As will be described and exemplified hereinafter, one of the major advantages of the process of the present invention for the recovery of ascorbic acid is that, after said stripping operation, the remaining organic extractant composition can be recycled, and further extraction carried out with said recycled organic extractant composition provides yields of at least 90%, and preferably at least 95%, ascorbic acid.

The invention will now be described in connection with certain preferred embodiments with reference to the attached figures, so that it may be more fully understood.

With specific reference now to the examples and distribution curves shown in the attached figures in detail, it is stressed that the particulars described and shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to provide details of the invention more than is necessary for a fundamental understanding of the invention, the description taken with the drawings making apparent to those skilled in the art how the several forms of the invention may be embodied in practice.

Figure 1:
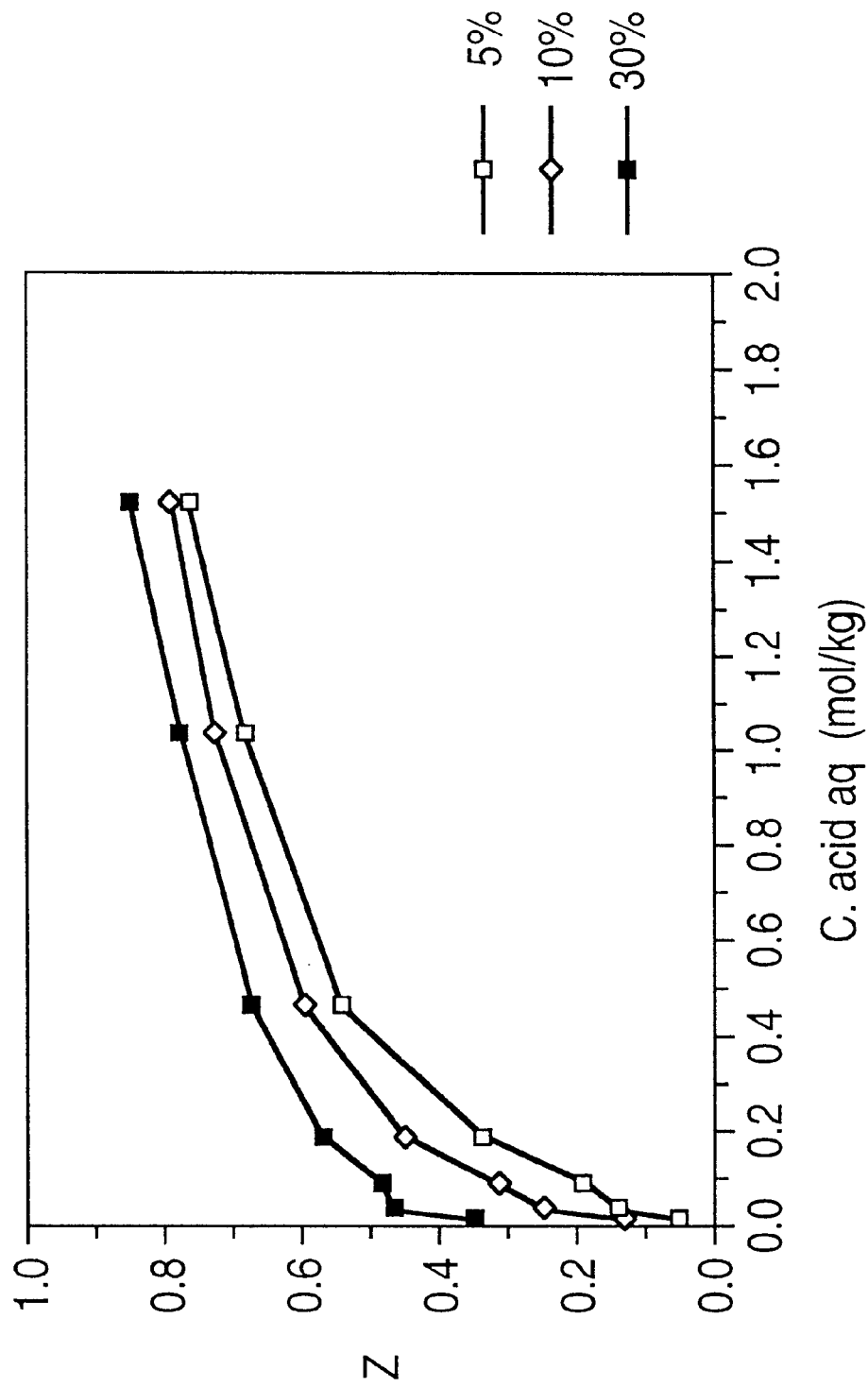
FIG. 1 is a distribution curve for citric acid extraction by tricaprylyl amine in kerosene, with various levels of octanol.

Referring to FIG. 1, wherein Z is the acid/amine molar ratio in the organic phase, it is seen that the extraction is enhanced by octanol, and the effect is particularly strong at the low concentration end.

Figure 2:
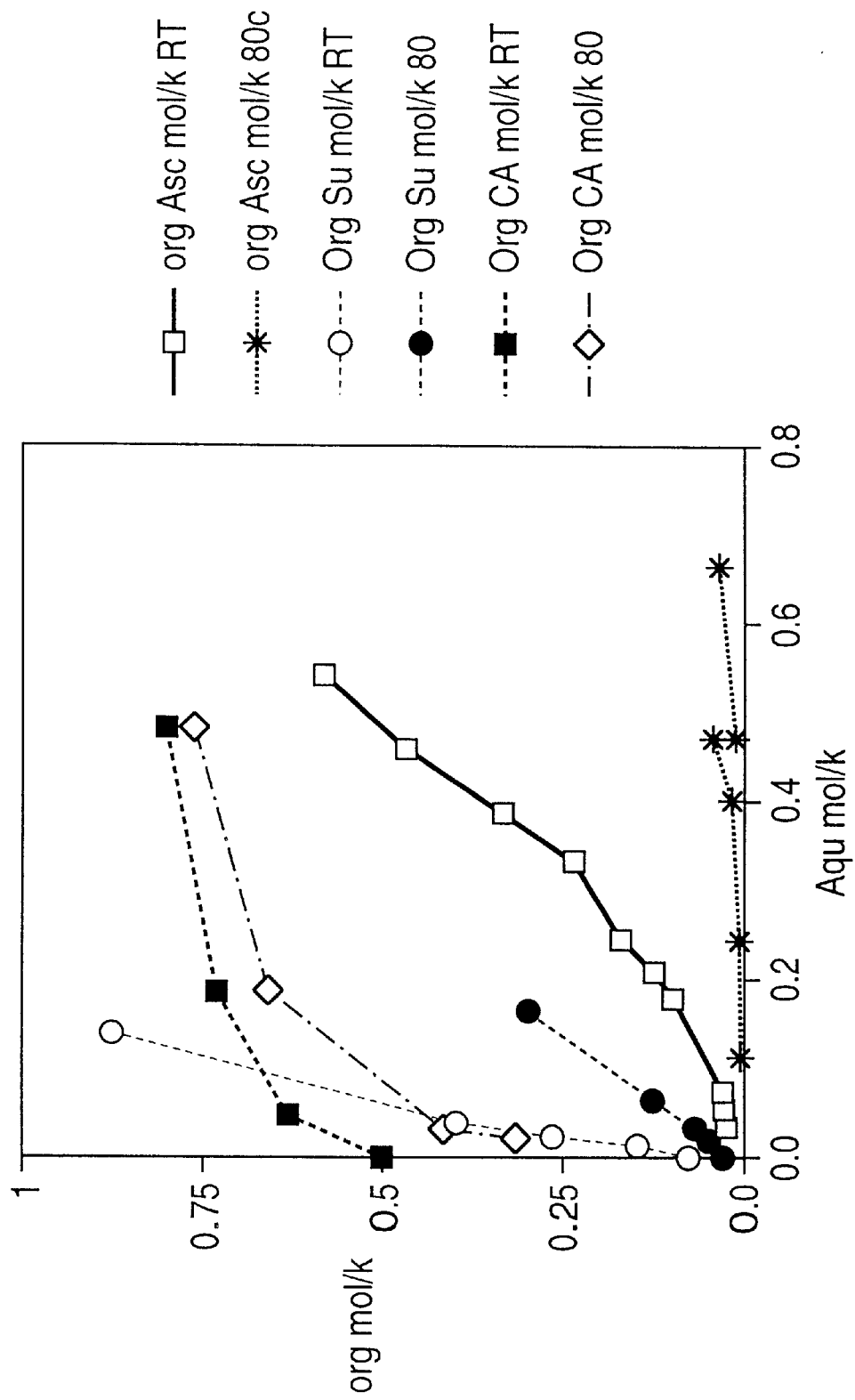
FIG. 2 shows distribution curves and temperature effect on different acids.

FIG. 2 shows distribution curves for extraction by an extractant composed of 1.2 mol/kg tricaprylyl amine and 2.4 mol/kg octanol in kerosene. Extraction of ascorbic acid at 25° C. from an 0.2 mol/kg solution can reach extractant loading of about 0.1 mol/kg. At 80° C., however, by extrapolating the bottom curve, this extractant loading of about 0.1 mol/kg is equivalent to 0.8 mol/kg ascorbic acid in the aqueous phase.

The result indicates that in using this extractant over the temperature gradient of 25–80° C., the uphill concentration factor for ascorbic acid is about 4. For citric acid and for succinic acid at these conditions, the factor is about 2. At this extractant composition, the TS for ascorbic acid is higher than those for citric acid and for succinic acid. Comparison with succinic acid was included herein in case one were to think that pKa is a factor in the results of the present invention, the pKa of succinic acid being the same as that of ascorbic acid.

As can be seen, however, the extraction for ascorbic acid is not yet sufficiently efficient and higher enhancer levels are preferred as described hereinafter with regard to FIG. 3.

Figure 3:
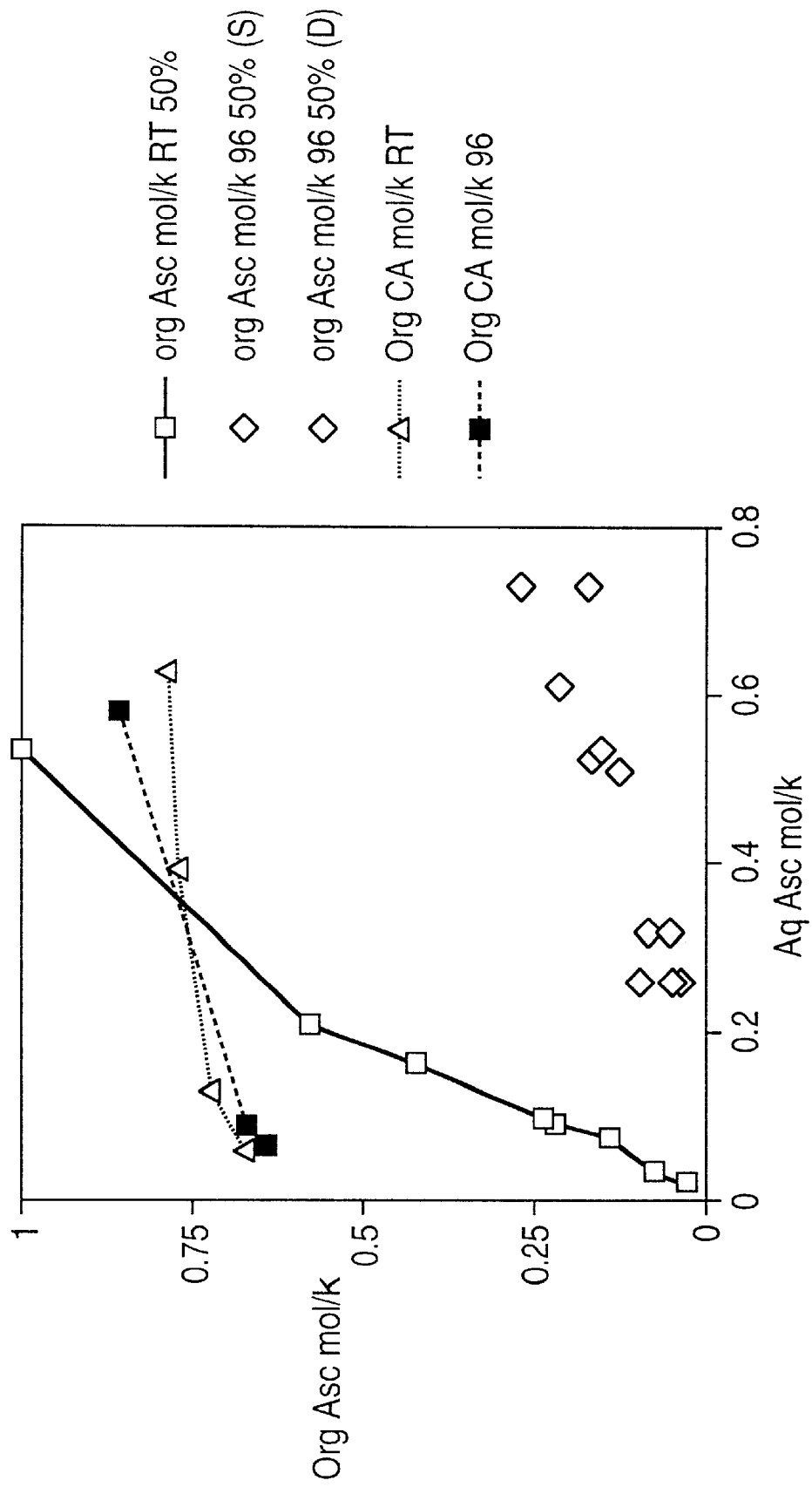
FIG. 3 shows comparative distribution curves for ascorbic and citric acid.

FIG. 3 illustrates distribution curves for extraction by an extractant composed of 1.2 mol/kg tricaprylyl amine (50%) and 3.8 mol/kg octanol (50%). The loading of the extractant in contact with 0.2 mol/kg ascorbic acid containing aqueous solution is about 0.5 mol/kg. Thus, increasing the content of the enhancer and avoiding the kerosene strongly enhanced the extraction, as compared to that shown in FIG. 2. The effect is even more impressive at the low concentrations end. The effect of the high enhancer level on the temperature sensitivity is surprisingly small. A concentration factor of about 4 can be reached on extraction at 25° C. and back-extraction at 96° C. Practically no temperature sensitivity is found for citric acid extraction at these conditions.

Figure 4:
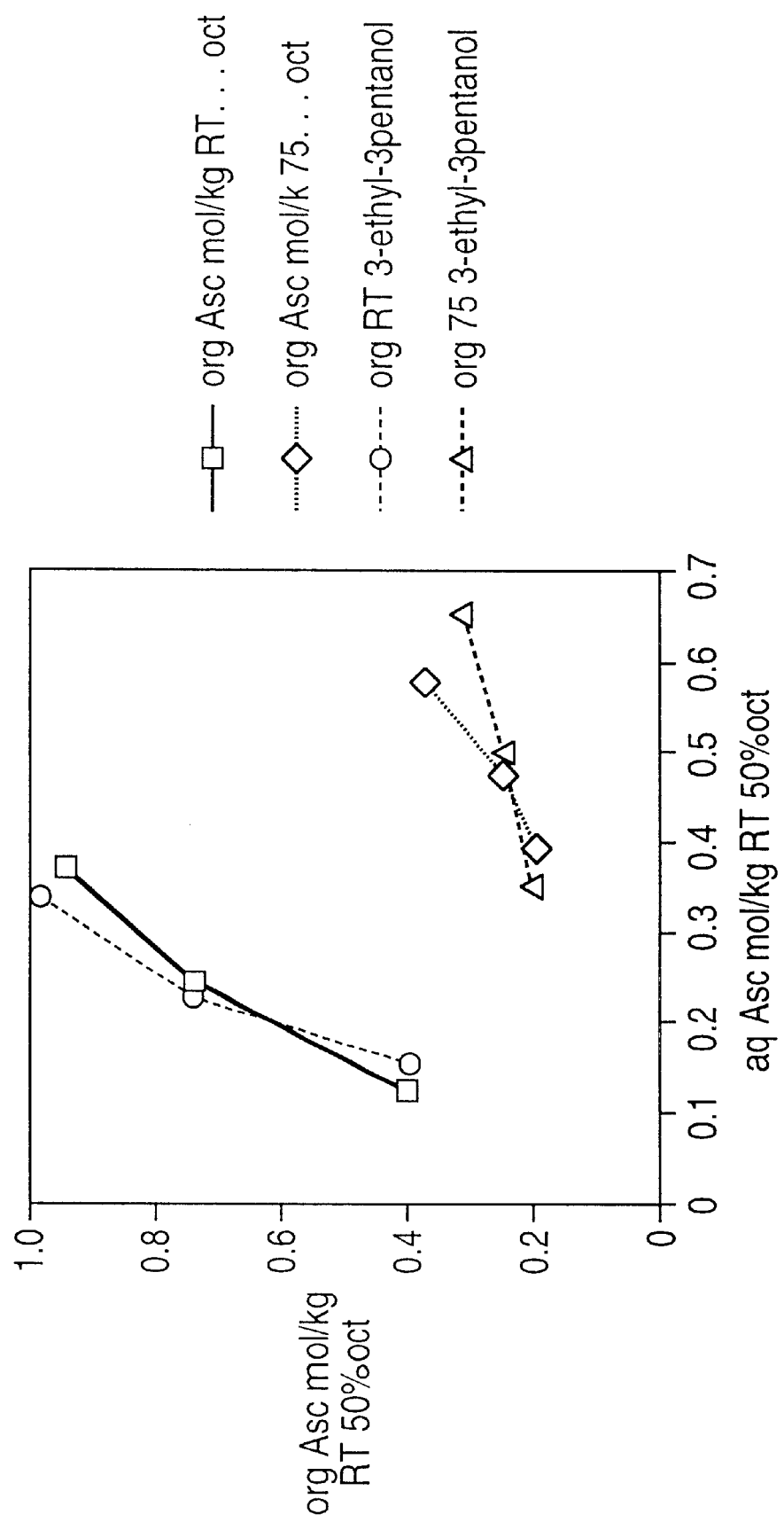
FIG. 4 is a distribution curve for ascorbic acid utilizing a non-sterically hindered extraction enhancer, as compared to a sterically-hindered, polar, organic, extraction enhancer compound of the preferred embodiments of the present invention.

Referring to FIG. 4, two extractants were tested. In both, the amine was tricaprylyl amine (Henkel's Alamine 336) and its concentration was 50 w/w %. In one of the extractant compositions, the enhancer was an octanol; in the other extractant composition, it was 3-ethyl-3-pentanol. In both cases, the enhancer content was 50% with no diluent having been used.

Distribution of ascorbic acid between water and these extractants was tested at ambient temperature and at 75° C. The results are shown in FIG. 4. As can be seen, the extraction at ambient temperature was similar for both extractants, or even slightly higher in the use of 3-ethyl-3-pentanol. At the elevated temperature, however, the extractant comprising 3-ethyl-3-pentanol was less efficient.

From the results of the test exemplified in FIG. 4, it can be realized that using a sterically hindered polar organic compound having at least 5 carbon atoms, a basicity weaker than that of the primary extractant, and temperature-sensitive, extraction-modifying properties as the extraction enhancer compound of the present invention, is indeed preferred.

Referring once again to the teachings of U.S. Pat. No. 4,275,234, it will be noted that several difficulties are indicated in the examples of said patent:

In most examples, no enhancer was used in the extractant, or it is used in a limited proportion of up to 5%. In Example 7, the extractant composition is 50% tri-tridecylamine and 50% nitrobenzene. Being a polar component, nitrobenzene is quite efficient as an enhancer. An extract containing 9.3% citric acid was back-extracted with water (100 g per 100 g of extract) at 60° C. (35° C. higher than the extraction temperature). Only 13% of the initial citric acid was back-extracted, forming a dilute solution of 13% citric acid. Adding 150 g hydrocarbon to dilute the amine and the enhancer was needed to improve the back-extraction. This example concluded that "the extract could not readily be back-extracted unless a hydrocarbon fraction was added to it." Addition of the hydrocarbon at the extraction step would have reduced its efficiency, as non-polar solvents act contrary to the enhancers and could be referred to as extraction inhibitors.

Example 16 of said patent describes the back-extraction of oxalic acid from an extractant composed of 25% w/w dilaurylbenzyl amine, 69% w/w n-octane and 6% 1-n-octanol. For efficient back-extraction, 50 g of n-octane were added to about 37 g of oxalic acid-containing extract. Thus, even at relatively low initial enhancer levels, substantial dilution by an extractant inhibitor was required. Only about 79% of the extracted acid is back-extracted at 80° C. Temperatures of 120–160° C. are recommended (Example 18).

The yield of lactic acid recovery from an initial solution comprising 1.1 mol/kg acid was 95% (Example 13). Enhancer-free extractant was used. The yield for $H_3PO_4$ recovery from an initial solution of 0.8 mol/kg was 88% (Example 14). Here again, no enhancer was used. The extraction yield for citric acid in Example 5 was 95%, using an extractant comprising 5% enhancer (octanol).

In said patent, there also appears in Example 12 a description of the extraction of dilute lactic acid in which high amounts of enhancer are ostensibly used with good results. According to the principles and theory of the present invention, the results obtained in Example 12 of U.S. Pat. No. 4,275,234 did not appear to be possible or correct. In order to clarify this point, the extraction of lactic acid from a 2% (0.22 mol/kg) solution and its stripping from the extractant were repeated as in Example 12. The extractant was composed of 50% w/w tridodecylamine and 50% w/w of 1-n-octanol. The extraction was conducted at 25° C. and the stripping at about 96° C.

Extraction as in Example 12 (100 g aqueous, 40 g extractant, 3 countercurrent stages) results in practically complete extraction of the acid to form an extract (loaded extractant) comprising 5% w/w lactic acid. Stripping as in Example 12 (40 g extract, 40 g water, 5 countercurrent stages) results in an aqueous solution comprising 0.7 g lactic acid in concentration of 1.8%. About two-thirds of the extracted lactic acid stays in the organic phase. Re-use of this organic phase in extraction from 2% lactic acid solutions results in low yields; not more than 20% of the acid is extracted. Increasing the number of stages in extraction has only a small effect. Near complete stripping and thus high yield in re-use of the organic phase requires about 150 g water per 40 g of extract, and 6–7 countercurrent stages. The lactic acid in this case is obtained in a dilute solution of about 0.5% w/w.

Thus, using an extractant comprising about 4 moles of enhancer per mole amine provides for nearly complete extraction of lactic acid from a dilute solution of 0.22 mol/kg, but on stripping, a high proportion of water is required and the acid is diluted 4 times, compared to its concentration in the feed. The cost of concentrating this solution is enormous.

Using the same extractant for extracting ascorbic acid from 0.22 mol/kg solution, 65 g of extractant per 100 g aqueous solution and 5–6 countercurrent stages, are required to reach an extraction yield of at least 95% at 25° C.

Stripping the extract at 96° C. with 35 g water results in an aqueous solution comprising 0.6 mol/kg ascorbic acid and an organic phase practically free of ascorbic acid. Re-use of this organic phase in extraction provides an extraction yield of at least 95% at the above conditions.

Thus, while in the case of lactic acid, practically complete extraction with recycled extractant results in a lactic acid product diluted 4 times compared with the feed, in the case of ascorbic acid at the same conditions and with similar extractant, practically complete extraction with recycled extractant results in ascorbic acid product solution concentrated 3 times compared with the feed.

Therefore, it is clear that one following the teachings of U.S. Pat. No. 4,275,234 and repeating the examples contained therein would come to the inescapable conclusion that the process taught therein is not suitable for the commercial production of ascorbic acid. Furthermore, said patent certainly does not teach or suggest the use of a stearicallyhindered, polar, organic, extraction enhancer compound as described and claimed herein.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the recovery of ascorbic acid from an aqueous feed solution containing said acid at a concentration of less than 0.7 mol/kg, comprising:

extracting said ascorbic acid with a water-immiscible organic extractant composition comprising (a) at least one secondary or tertiary alkyl amine in which the aggregate number of carbon atoms is at least 20, as a primary extractant, and (b) a polar extraction enhancer compound;

wherein said extractant composition comprises at least 2 moles of said polar extraction enhancer compound per one mole of primary extractant;

separating said ascorbic acid-containing organic extractant composition from residual aqueous solution, and subjecting said ascorbic acid-containing organic extractant composition to a stripping operation with aqueous solution at a temperature of at least 20° C. higher than the temperature at which said extraction is carried out;

whereby there is obtained an aqueous solution of ascorbic acid in which the concentration of ascorbic acid is higher than its concentration in said aqueous feed solution.

2. A process for the recovery of ascorbic acid as claimed in claim 1, wherein said extractant composition comprises at least 3 moles of said extraction enhancer compound per one mole of primary extractant.

3. A process for the recovery of ascorbic acid as claimed in claim 1, wherein said stripping action effects the back-extraction of at least 80% of the ascorbic acid contained in said organic extractant composition.

4. A process for the recovery of ascorbic acid as claimed in claim 1, wherein, after said stripping operation, the remaining organic extractant composition is recycled.

5. A process for the recovery of ascorbic acid as claimed in claim 4, wherein further extraction carried out with said recycled organic extractant composition provides yields of at least 90% ascorbic acid.

6. A process for the recovery of ascorbic acid as claimed in claim 4, wherein further extraction carried out with said recycled organic extractant composition provides yields of at least 95% ascorbic acid.

7. A process for the recovery of ascorbic acid as claimed in claim 1, wherein said aqueous feed solution contains said acid at a concentration of less than 0.5 mol/kg.

8. A process according to claim 1, for the recovery of ascorbic acid from an aqueous feed solution containing said acid at a concentration of less than 0.7 mol/kg, comprising extracting said ascorbic acid with a water-immiscible organic extractant composition comprising:

(a) at least one secondary or tertiary alkyl amine in which the aggregate number of carbon atoms is at least 20, as a primary extractant, and (b) a sterically hindered, polar, organic, extraction enhancer compound having at least 5 carbon atoms, a basicity weaker than that of said primary extractant, and temperature-sensitive, extraction-enhancing properties;

wherein said extractant composition comprises at least 2 moles of said extraction enhancer compound per one mole of primary extractant;

separating said ascorbic acid-containing organic extractant composition from residual aqueous solution, and subjecting said ascorbic acid-containing organic extractant composition to a stripping operation with aqueous solution at a temperature of at least 20° C. higher than the temperature at which said extraction is carried out;

wherein said extraction enhancer compound both enhances the extracting power of said primary extractant composition and facilitates said temperature-sensitive stripping operation, and whereby there is obtained an aqueous solution of ascorbic acid in which the concentration of ascorbic acid is higher than its concentration in said aqueous feed solution.

9. A process according to claim 8, wherein said sterically hindered, polar, organic, extraction enhancer compound is selected from the group consisting of alkanols, carboxylic acids, tertiary amines, or trialkylphosphates having a sterically hindering substituent attached to the carbon carrying said polar group, or to a carbon which is alpha, beta, or gamma to said carbon.

10. A process according to claim 9, wherein said substituent is an aliphatic group.

11. A process according to claim 8, wherein said extraction enhancer compound is selected from the group consisting of secondary or tertiary alkanols, tris-2-ethylhexyl amine, and tris-2-ethylhexyl phosphate.

12. A process according to claim 1, wherein the aqueous feed solution of ascorbic acid is obtained by fermentation.

13. An extractant composition for use in a process for the recovery of ascorbic acid from an aqueous solution containing said acid or a salt thereof, said composition comprising:

a) at least one secondary or tertiary alkyl amine in which the aggregate number of carbon atoms is at least 20, as a primary extractant; and b) a sterically hindered, polar, organic compound having at least 5 carbon atoms, a basicity weaker than that of said primary extractant, and temperature-sensitive, extraction-enhancing properties.

14. An extractant composition as claimed in claim 13, further comprising a water-immiscible, organic solvent.

* * * * *